United States Patent [19]

Kirsch et al.

[11] Patent Number: 5,294,725
[45] Date of Patent: Mar. 15, 1994

[54] SCOPULARIN

[75] Inventors: Donald R. Kirsch, Princeton; Joseph O'Sullivan, Belle Mead; Douglas W. Phillipson, Princeton, all of N.J.

[73] Assignee: E. R. Squibb & Sons, Inc., Princeton, N.J.

[21] Appl. No.: 305,338

[22] Filed: Jan. 31, 1989

[51] Int. Cl.$^5$ ............................................. C07D 309/10
[52] U.S. Cl. ...................................................... 549/417
[58] Field of Search .................. 549/417; 514/459, 460

[56] References Cited
U.S. PATENT DOCUMENTS
4,952,604  8/1990  Hensens et al. ..................... 514/459

FOREIGN PATENT DOCUMENTS
56-18592  2/1981  Japan .

OTHER PUBLICATIONS
R. Schwartz et al., *Journal of Antibiotics*, vol. 44, No. 5, 463, (1991).

Primary Examiner—Nicky Chan
Attorney, Agent, or Firm—Theodore R. Furman, Jr.; Ellen K. Park

[57]  ABSTRACT

A novel antibiotic substance, Scopularin, is prepared by cultivation of a strain of the microorganism, Scopulariopsis, A.T.C.C. No. 20,914. This compound and its alcohol derivative have also been found to have cytochrome P450 inhibition activity.

1 Claim, 8 Drawing Sheets

SCOPULARIN

SUMMARY OF THE INVENTION

Cultivation of a strain of the microorganism Scopulariopsis sp. which has been deposited in the American Type Culture Collection as A.T.C.C. No. 20,914 yields a novel antibiotic substance hereinafter referred to by the trivial chemical name "scopularin". The antibiotic has activity against a variety of yeasts and fungi, and has also been found to inhibit cytochrome P450 enzymes, such as lanosterol demethylase. An alcohol derivative of scopularin is also an inhibitor of cytochrome P450 enzymes, such as lanosterol demethylase.

Scopularin has been analyzed and found to have the general chemical structure

I wherein R is and the present invention further includes the alcohol derivative of scopularin, that is, where R is hydrogen.

DETAILED DESCRIPTION OF THE INVENTION

The Microorganism

The microorganism used for the production of scopularin is a strain of Scopulariopsis isolated from a soil sample collected from St. Paul's Gate, Rome, Italy. A subculture of the organism can be obtained from the American Type Culture Collection, Rockeville, Md. Its accession number in this repository is A.T.C.C. No. 20,914. In addition to the specific microorganism described and characterized herein, it should be understood that mutants of the microorganism produced through the use of chemical or physical mutagens can also be cultivated to produce the subject compound.

The microorganism can be isolated from a soil sample in which it is present by placing 0.5 gram of the soil in 10 ml of the following sterile buffer:

| | |
|---|---|
| NaCl | 8.5 g |
| KH$_2$PO$_4$ | 0.3 g |
| Na$_2$HPO$_4$ | 0.6 g |
| Gelatin | 0.1 g |
| Distilled Water to | 1000 ml |

The sample is mixed by vortexing and then sonicated for 10 minutes in an ultrasonic water bath. A series of dilutions are then prepared in the above buffer and 0.1 ml aliquots of the dilutions are spread-plated onto the following agar medium in order to obtain isolated colonies:

| | |
|---|---|
| Yeast extract | 2.0 g |
| Glucose | 5.0 g |
| Oxgall | 5.0 g |
| Sodium propionate | 1.0 g |
| CaCO$_3$ | 3.0 g |
| Agar | 2.0 g |
| V-8 Juice | 2 ml |
| Distilled Water | 800 ml |
| pH adjusted to | 6.8 |

The medium is autoclaved at 121° C. for 15 minutes. Chlorotetracycline (30 mg/liter) and streptomycin (30 mg/liter) are added to the medium before dispensing into petri dishes.

After 5 days inculation at 25° C., colonies of Scopulariopsis sp. A.T.C.C. No. 20,914 are isolated from the plated samples. The isolated colonies are then grown on potato dextrose agar.

Colonies of Scopulariopsis sp. on potato-dextrose agar (PDA) grow rapidly with the leading edge of growth submerged in the agar. Surface growth from the center out is zonate with alternating bands of pinkish-buff to avellaneous (grey tinged with pink) in color. The reverse is brownish-orange with the center a deep burgundy red. The surface texture is lanose (wooly) with sporulation covering the agar plate. A deep burgundy exudate is produced on the aerial mycelium which upon drying produces craters giving the mycelial mat a pock-marked appearance.

On cornmeal agar growth of Scopulariopsis sp. is thin transparent and pinkish-grey in color. The reverse color is a mouse grey. Surface texture is lanose with droplets of colorless exudate clinging to aerial hyphae. With age the exudate becomes a burgundy red color tingeing the underlying agar. Heavy sporulation gives the culture a salt and pepper appearance. There is no evidence of formation of coremia or perithecia.

Hyphae of Scopulariopsis sp. are hyaline (colorless) when young, irregularly becoming fuscous (brownish-grey) with age. They are 1.5–2 μm in diameter. Sporulation occurs from the terminus of annellophores which are flask-shaped structures tapering to a narrow opening. Annellophores may occur singly or in verticils of 3–4 on the end of short hyphae. They average 4.5×2 μm in size.

The spores are produced within the annellophore by successive division of a mother nucleus and pass through this opening forming chains of varying length.

Each successive spore formed leaves a characteristic scar on the outer wall of the annellophore. Spores are thick-walled with a truncate base occasionally with a small collarette attached. They are spherical to subovate, smooth and 3 μm in diameter. When first formed they appear smooth becoming rough with age. They have a longitudinal line which in fact is a thin-walled slit through which the germ tube passes at germination.

The following key diagnostic characters provide the basis for assigning the producing organism to the form-genus Scopulariopsis.

1. absence of coremia or perithecia;
2. annellidic sporulation;
3. presence of scars on the outer wall of the annellophore;
4. spore germination through a longitudinal germinal slit;
5. spores with truncate ends separated by a collarette;
6. spores borne in chains.

The Antibiotic Scopularin

The antibiotic scopularin can be produced by cultivating Scopulariopsis sp. A.T.C.C. No. 20,914 at, or near, 25° C. under submerged aerobic conditions in an aqueous nutrient medium containing assimilable carbohydrate and nitrogen sources. The fermentation is carried out until substantial activity is imparted to the medium, usually about 72 to 76 hours.

After three days the broths are pooled and filtered. The cell mass is extracted with methanol and the concentrated methanol extract is chromatographed on silica gel eluting with a methanol-chloroform step gradient. Final purification of the active fraction from the silica gel column is achieved using an Ito counter current chromatography coil with a heptane-ethyl acetate-methanol-buffer system.

Alternatively, the whole broth may be extracted with ethyl acetate and the concentrated organic phase partitioned in ethyl acetate/methanol/water (5:2:5). The activity partitions into the lower phase while most of the mass remains in the upper phase. After removal of the methanol in vacuo from the lower phase, the activity is re-extracted into ethyl acetate. The concentrated ethyl acetate layer is purified using the Ito and silica gel steps mentioned above.

Figure 1:
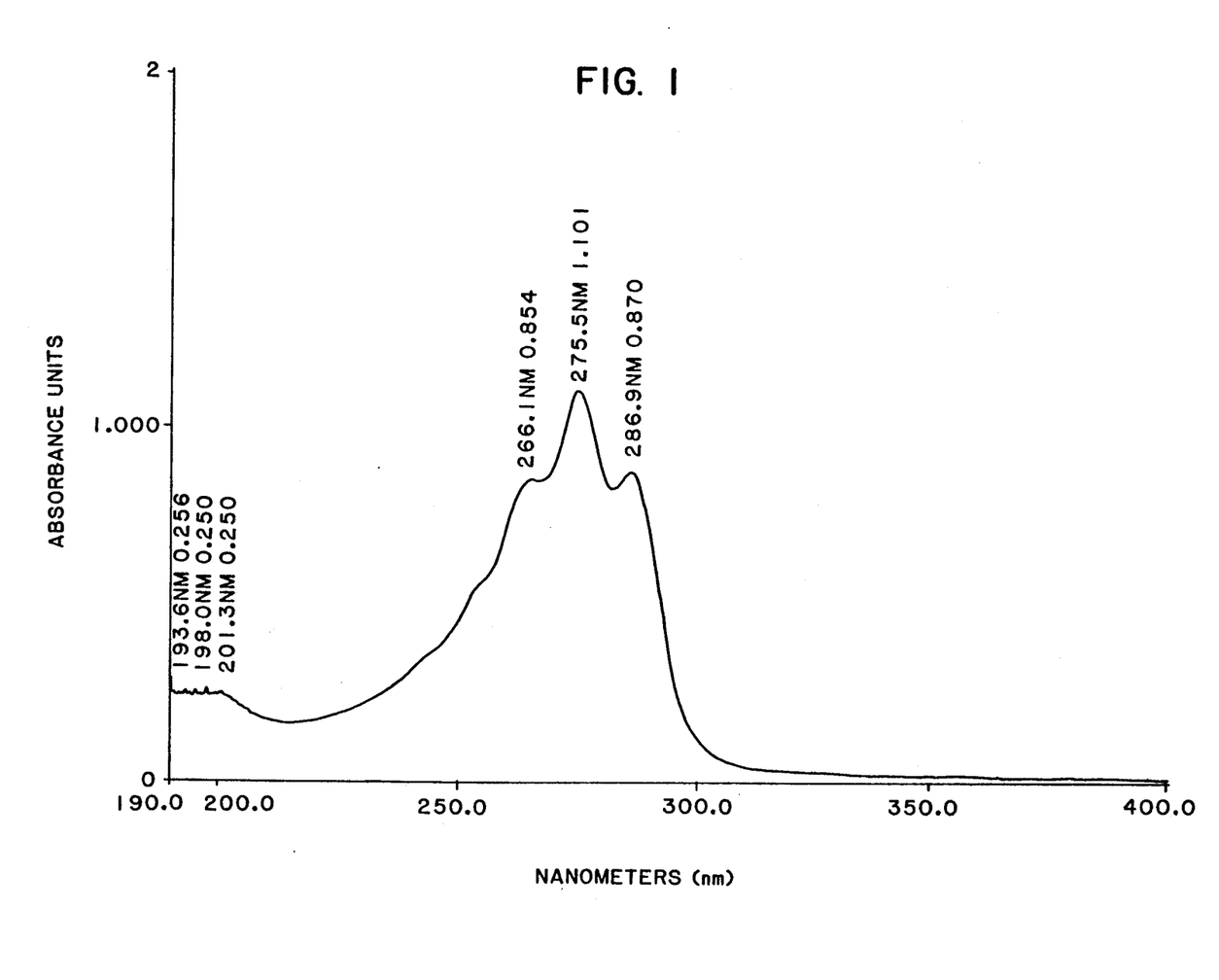
FIG. 1 is the ultraviolet spectrum of scopularin recorded in methanol.
Figure 2:
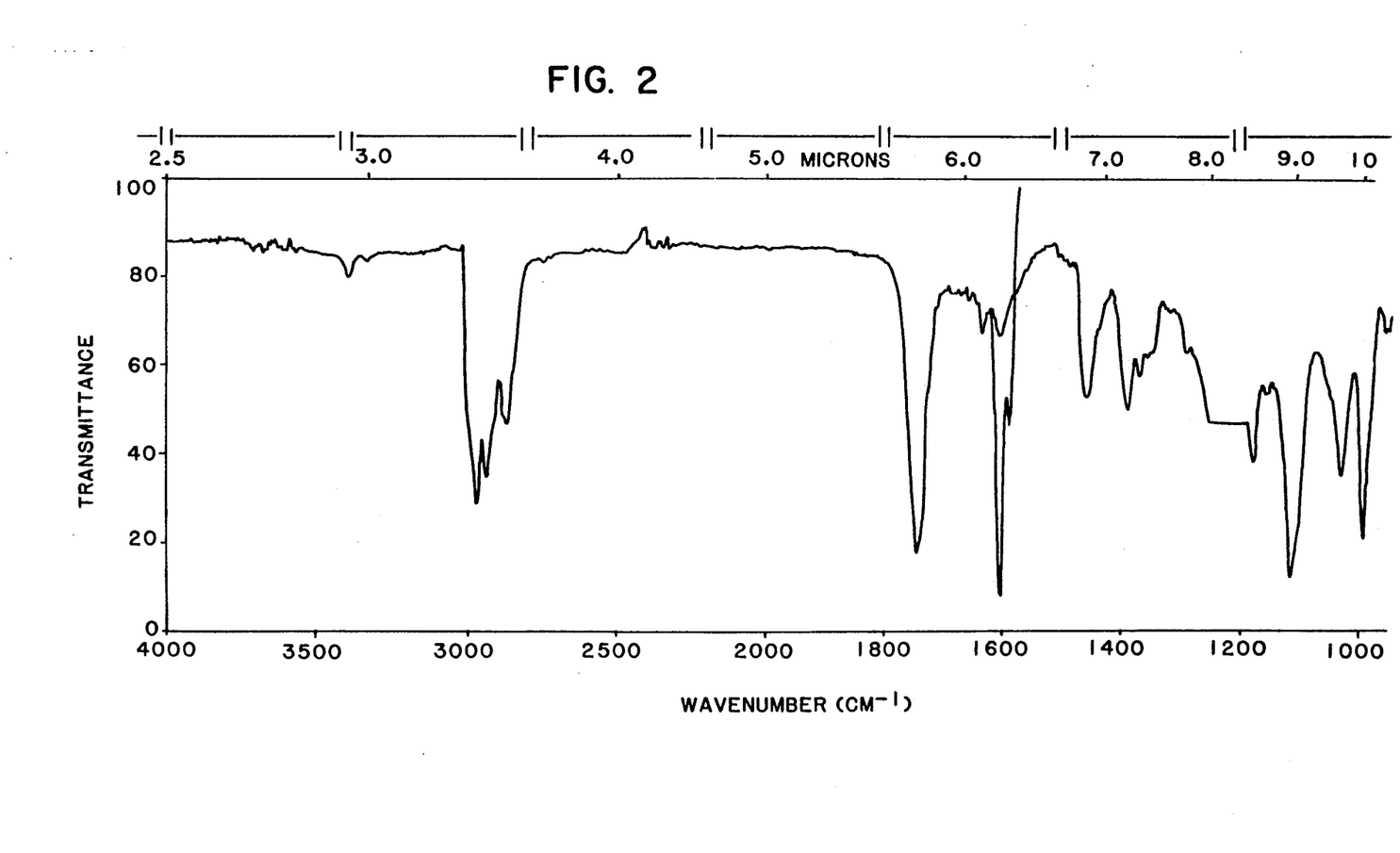
FIG. 2 is the infrared spectrum of scopularin recorded in chloroform.
Figure 3:
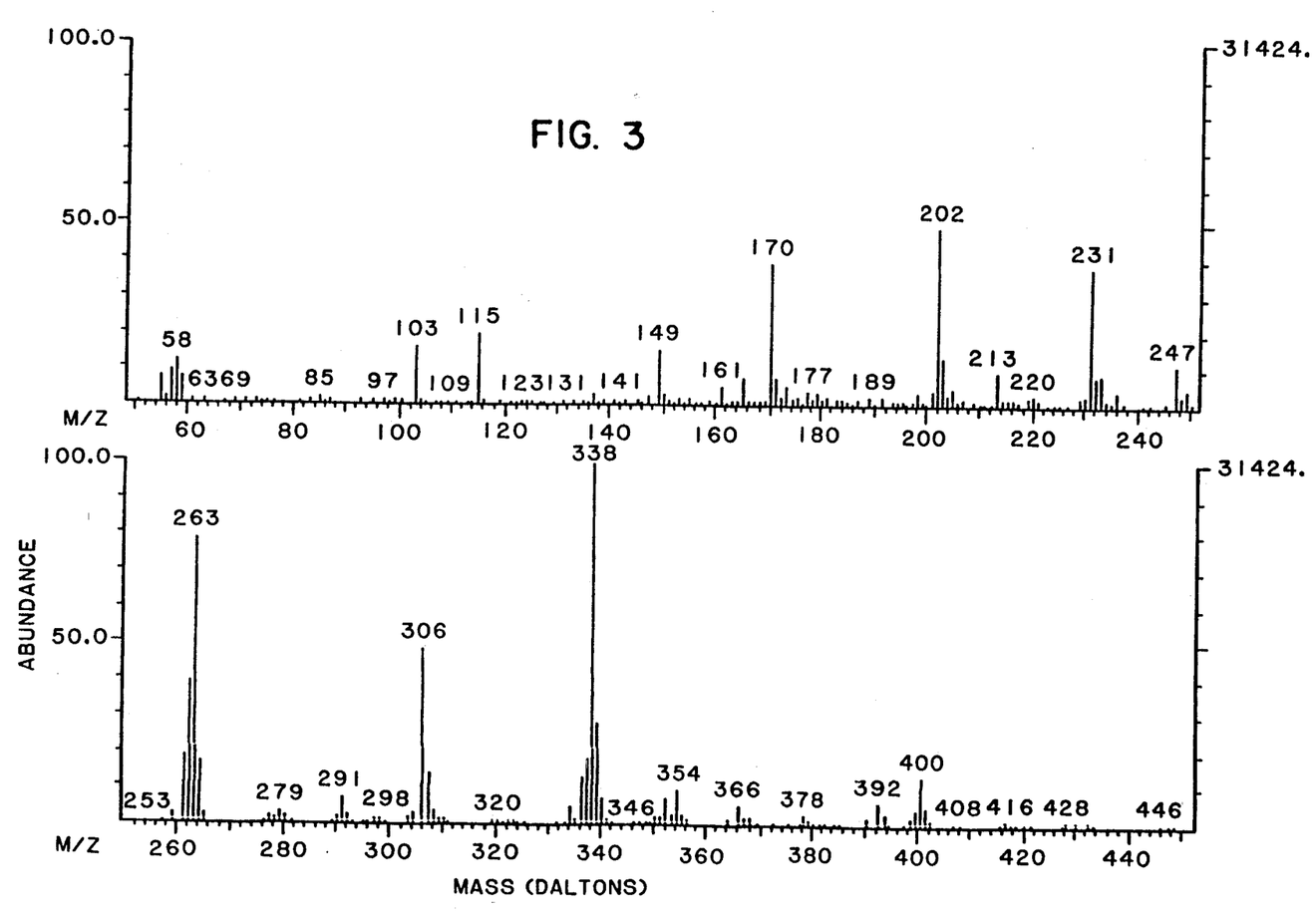
FIG. 3 is the positive ion chemical ionization mass spectrum of scopularin.
Figure 4:
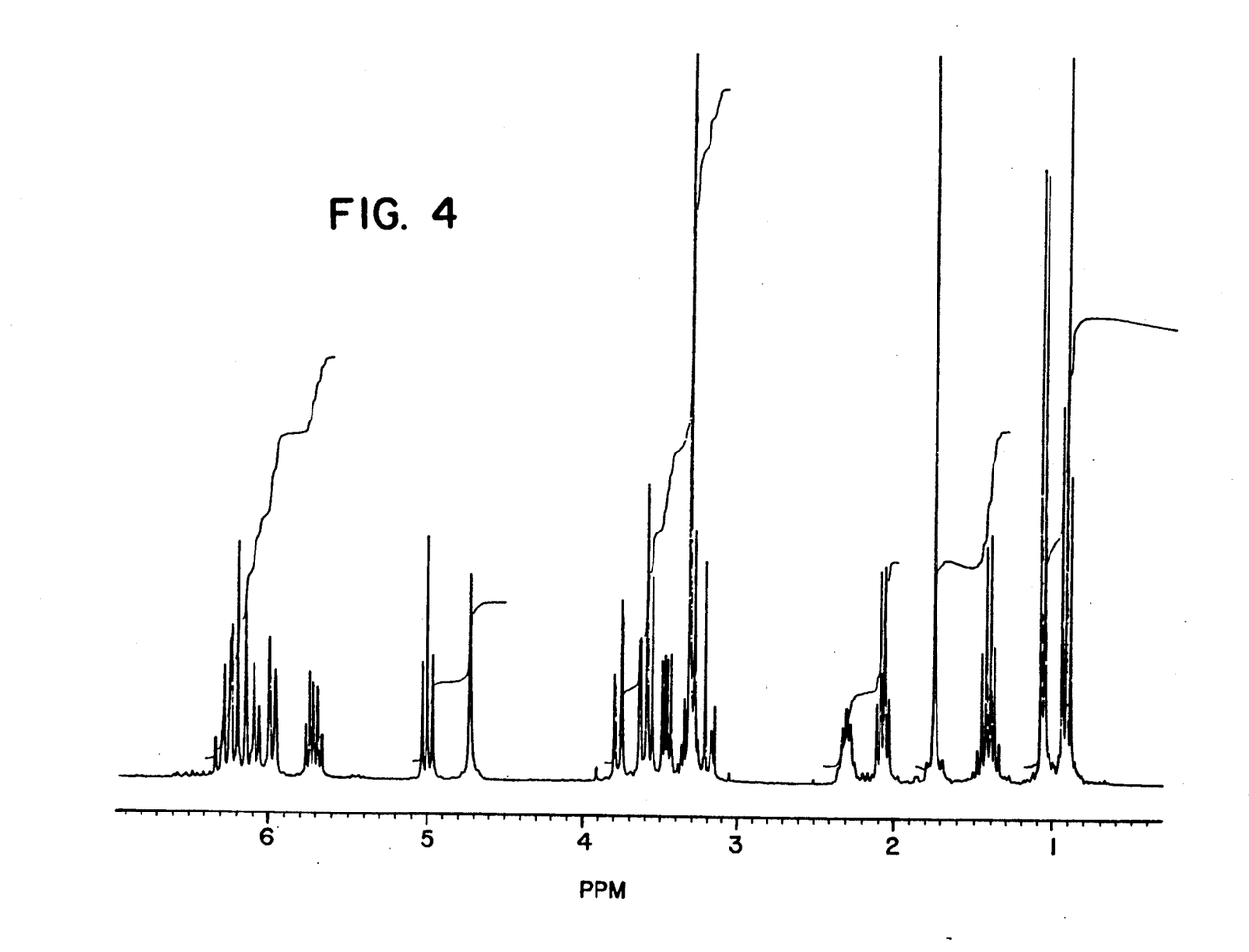
FIG. 4 is the 270 MHz $^1$H NMR spectrum of scopularin recorded in the deuteromethanol.
Figure 5:
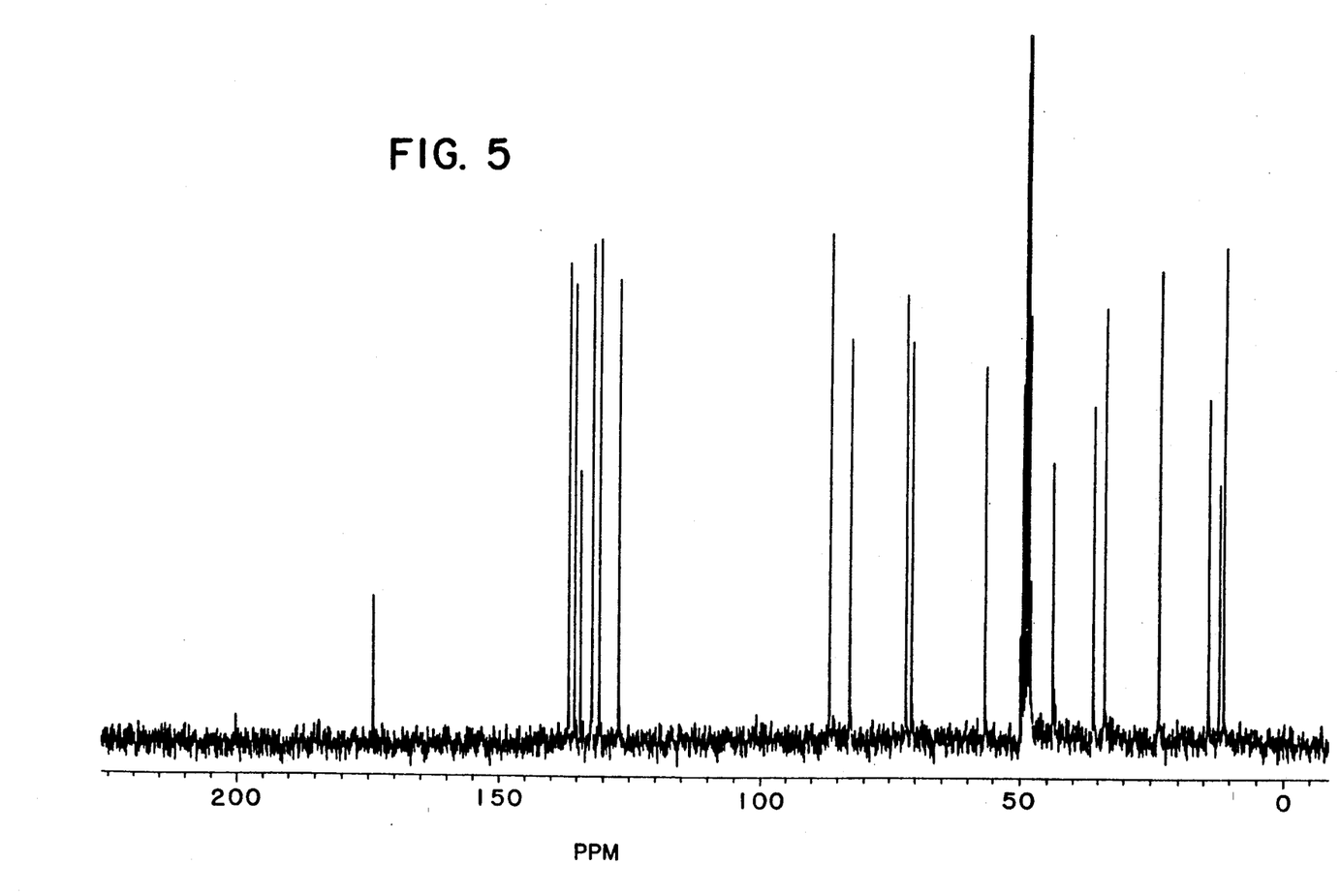
FIG. 5 is the 67.5 MHz $^{13}$C NMR spectrum of scopularin recorded in deuteromethanol.

The UV spectrum of scopularin, recorded in methanol, has an absorption maximum at 275 nm with an extinction coefficient of 37,000. Shoulders on the main band can be seen at 266 and 286 nm. The UV spectrum of scopularin is shown in FIG. 1. There were no observable changes in the spectrum when recorded in acid or base. The Infra-red spectrum recorded in chloroform is reproduced as FIG. 2. Prominent bands are observable at 2970, 2940, 2860, 1740, 1460, 1390, 1115, 1030 and 990 cm$^{-1}$. The positive ion chemical ionization mass spectrum is given in FIG. 3. In addition to the pseudomolecular ion at 338 daltons, other fragment ions can be observed at m/z 306, 263, 231, 202 and 170. A high resolution mass measurement of the [M+H]$^+$ ion in the Fast Atom Bombardment mass spectrum yielded a value of 338.2310. The exact mass calculated for the formula $C_{19}H_{32}NO_4$ is 338.2331. The 270 MHz proton spectrum recorded in deuteromethanol is depicted in FIG. 4. The 67.5 MHz carbon spectrum (also recorded in deutero methanol solution) is given in FIG. 5. The resonances and multiplicities determined from INEPT spectra (not shown) are as follows: 174.12(s), 136.54(d), 135.42(d), 134.27(s), 132.08(d), 130.75(d), 127.01(d), 86.61(d), 82.78(d), 71.75(t), 70.71(d), 56.63(q), 43.90(t), 35.96(t), 33.71(d), 23.54(t), 13.98(q), 11.88(q), 11.08(q).

Scopularin has a TLC $R_f$ of 0.4 when chromatographed on E. Merck Kieselgel 60 $F_{254}$ 5×10 cm plates using a chloroform/methanol (19:1) solvent system. An HPLC system consisting of a Varian 5020 LC, Spectra-Physics 4290 integrator, Perkin-Elmer CR $C_{18}$ 3×3 column, 1 mL/min. flow rate, with acetonitrile as the organic modifier and a 0.1M ammonium acetate (adjusted to pH 4.5 with acetic acid) buffer system, UV detection at 260 nm, was used. With a gradient composed of the following program of linear segments; T =0, 30 μOrganic, T=5 min. , 50%, T =9.5 min., 100%, hold at 100% till 12 min. then back to 30% at 13 min., re-equilibrate at 30% for 3.5 min. between injections, scopularin has a retention time of approximately 6.6 min.

Scopularin, and pharmaceutically acceptable salts thereof, can be used to combat fungal infections (particularly infections of Candida and other yeasts and filamentous fungi, such as Tricophyton, Microsporum, Aspergillus, etc.) in domesticated animals and humans. In addition, scopularin, including pharmaceutically acceptable salts thereof, inhibits cytochrome P450 enzymes, such as lanosterol demethylase. It has also been found that the alcohol derivative of scopularin (i.e, the compound of formula I where R is hydrogen) is an inhibitor of cytochrome P450 enzymes, such as lanosterol demethylase, as well. These compounds can therefore be used in a variety of ways including as an adrenal steroidogenesis inhibitor for the treatment of metastatic mammary carcinoma, in post-menopausal or ovariectomized women, in Cushing's syndrome, in breast, prostatic, endometrial, ovarian and pancreatic carcinomas, and as an inhibitor of aromatase or other cytochrome P450 enzymes. Based on this cytochrome P450 inhibition activity, the compounds of the present invention are also expected to be useful in the treatment of hypertension. These compounds can be administered topically, orally or parenterally. The dosage used of scopularin, a pharmaceutically acceptable salt thereof, or the alcohol derivative thereof will vary with the severity of the infection or disorder and the size of the host. For a human adult, daily doses of about 100 mg to 1 gm/day are exemplary. Information relating to the potency of scopularin and its alcohol derivative is set forth below under the heading "Biological Activity".

Scopularin, or salts thereof, may also be used in the treatment of fungal diseases of plants. Scopularin and the alcohol thereof may also be used as a plant growth regulator by inhibition of cytochrome P450 monooxygenases involved in the biosynthesis of gibberellin. Treatment with Scopularin, the alcohol or salts thereof, may be carried out by application to seed, foliage or to the soil.

The following examples further illustrate the preparation and utility of scopularin and its alcohol derivative.

EXAMPLE 1

Scopulariopsis sp. A.T.C.C. No. 20,914 was maintained on the following sterilized agar medium (A):

| | |
|---|---|
| Malt Extract | 10.0 g |
| Yeast Extract | 10.0 g |
| Peptone | 1.0 g |
| Dextrose | 20.0 g |
| Agar | 15.0 g |

| -continued | |
|---|---|
| Distilled Water to | 1000 ml |

The pH was adjusted to 7.0 and the medium was sterilized at 121° C. for 20 minutes.

A loopful of surface growth from agar slants (Medium A) of Scopulariopsis sp. was used to inoculate each of five 500 ml Erlenmeyer flasks each containing 100 ml of the following sterilized medium (B):

| Toasted Nutrisoy Flour | 15.0 g |
|---|---|
| Soluble Starch | 15.0 g |
| Glucose | 50.0 g |
| $CoCl_2 \cdot 6H_2O$ | 0.005 g |
| $CaCO_3$ | 10.0 g |
| Distilled Water to | 1000 ml |

After inoculation, the flasks were incubated at 25° C. on a rotary shaker (300rpm; 2 inch stroke) for approximately 72 hours with a resulting broth pH 6.0–6.5. Transfers of 4% (vol./vol.) were made from the grown culture flasks to one hundred 500 ml Erlenmeyer flasks each containing 100 ml of sterilized medium C: (Medium C was Medium A described above without the addition of agar). After inoculation, the flasks were once again incubated at 25° C. on a rotary shaker (as previously described) for approximately 72 hours with a resulting broth pH of 6.0–6.5. At this time, the contents of the flasks were pooled and the broth was filtered. The cell mass (2.0 kg) obtained was extracted twice with 2 L portions of methanol (1 hour for each extraction) and the extract concentrate (ca. 4.5×) was isolated.

Examples 2 and 3, which follow, outline typical isolation techniques used for isolation of Scopularin after fermentation as described above.

EXAMPLE 2

After the fermentation was completed, the pooled whole broth was filtered and the cell cake, consisting of 500 mL of wet cells, was extracted with 2×1 L portions of methanol, stirring the suspension for one hour with each pass. The combined methanol extracts were concentrated to 100 mL and this aqueous residue was lyophilized. The resulting oil was redissolved in a minimum of methanol and applied to the head of a 2.5×15 cm column packed with Merck silica gel and equilibrated with heptane. The column was eluted with 2 L of ethyl acetate/heptane (1:9) followed by 1 L portions of methanol/chloroform (1:200) followed by (1:100) followed by (1:50). Twenty five mL fractions were collected and assayed by TLC. (TLC $R_f$ of 0.4 on E. Merck Kieselgel 60 $F_{254}$ 5×10 cm plates with a methanol/chloroform (1:19) solvent system). Fractions containing Scopularin by TLC were pooled and the solvent removed. The active fraction from the silica gel column was loaded onto the head of an Ito Multi-Layer Coil Separator-Extractor (P. C. Inc., Potomac, Md.) which was filled with the lower phase of a heptane/ethyl acetate/methanol/buffer (0.1M ammonium acetate adjusted to pH 4.5 with acetic acid) (1:1:1:1) system. The coil, a multilayer teflon tubing (1.6 mm, i.d.) with a volume of 330 mL, was spun at 800 rpm and the upper phase of the solvent system was pumped through the coil at 4 mL/min. and collected in 5 minute fractions. Pure scopularin eluted in fractions 32–46. These fractions were pooled and the solvent evaporated to yield 15 mg of pure (2α, 3β, 4α, 5α)-Tetrahydro-4-methoxy-5-methyl-2-(1-methyl-1,3,5-nonatrienyl)-2H-pyran-3-ol, amino-acetate ester.

EXAMPLE 3

The pooled whole broth from a 10 L fermentation was extracted with 2, five L portions of ethyl acetate and the combined organic layers were concentrated to an oil and taken up in a small volume of methanol for storage in a freezer. The extracts from five 10 L batches were pooled and concentrated to an oily residue and this residue re-dissolved in 100 mL methanol. Fifty mL of the pooled extract was shaken with an additional 50 mL methanol and 250 mL ethyl acetate and 250 mL water. After removal of the aqueous layer, the organic phase was re-extracted with two additional 250 mL portions of lower phase from the ethyl acetate/methanol/water (5:2:5) solvent mixture. The combined aqueous phases were concentrated to approximately 100 mL in vacuo and extracted with 3×100 mL portions of ethyl acetate. The combined ethyl acetate phases were concentrated to dryness. The above extraction procedure was performed on the remaining 50 mL of methanol concentrate and the final ethyl acetate concentrates were combined. This material was purified using the Ito and silica gel steps as given above to yield 70 mg pure scopularin.

The following example illustrates synthesis of the alcohol derivative of scopularin.

EXAMPLE 4

Alcohol Derivative of Scopularin

The alcohol of scopularin is easily prepared from scopularin by basic hydrolysis of its ester linkage. For example, 60 mg of scopularin was dissolved in 2 mL methanol. 1 mL of saturated, sodium carbonate solution was added and the mixture was allowed to stir. After 2 hours the reaction was complete as judged by TLC. (The alcohol has an $R_f$ of 0.4 on Merck silica gel plates, using ethyl acetate/heptane (2:3) as the developing solvent, and may be visualized using short wave ultraviolet light, $I_2$, phosphomolybdic acid, vanillin/$H_2SO_4$, and other reagents sensitive to olefins and hydroxyl groups.) The mixture was diluted with 20 mL $H_2O$ and the resulting solution was extracted three times with 50 mL portions of dichloromethane. The combined organic extracts were dried over sodium sulfate, concentrated and chromatographed on a 20 g silica gel column using ethyl acetate/heptane (15:85) as the eluting solvent. Five mL fractions were collected and examined by TLC. Fractions containing pure alcohol were pooled and the solvent evaporated to yield 40 mg, 80% of the theoretical yield of scopularin alcohol.

Figure 6:
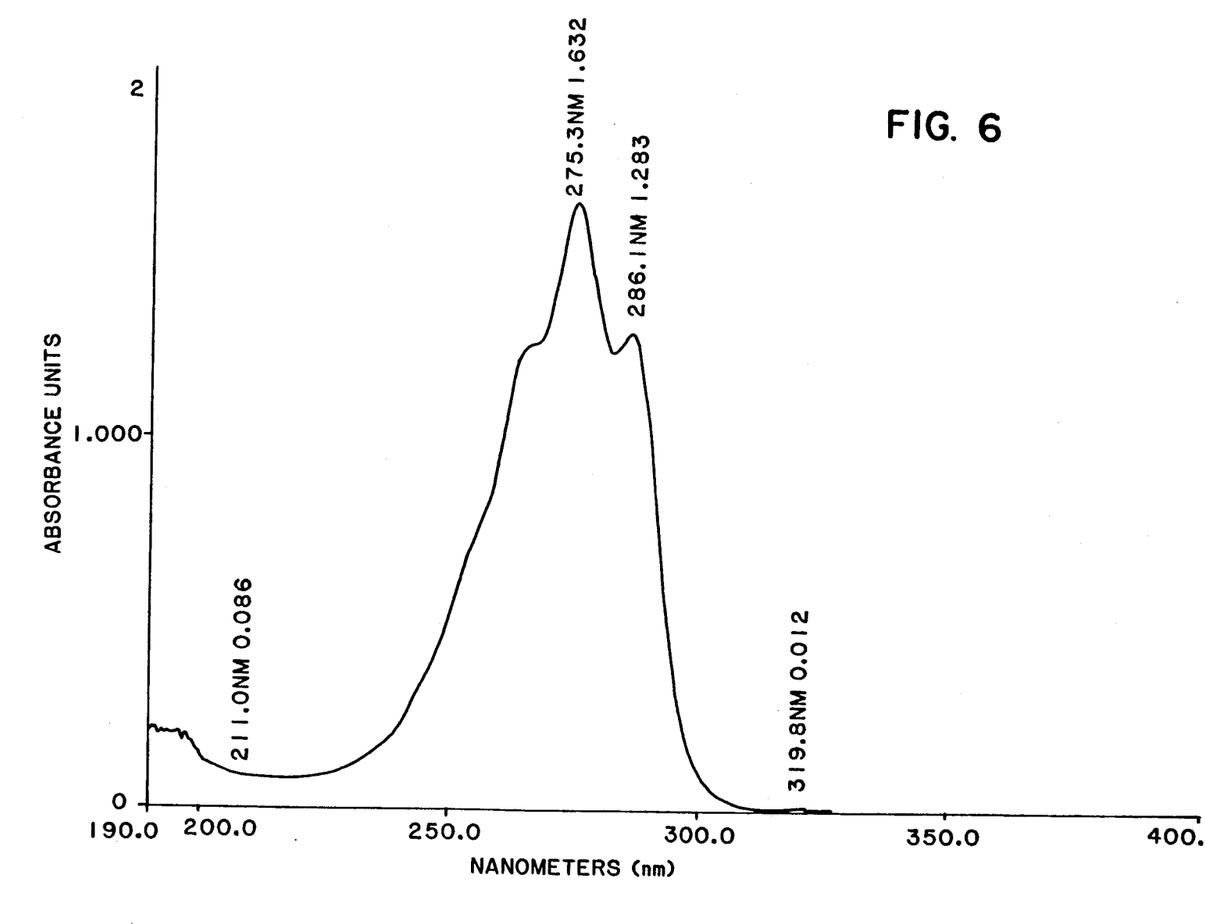
FIG. 6 is the ultraviolet spectrum of scopularin alcohol recorded in methanol.
Figure 7:
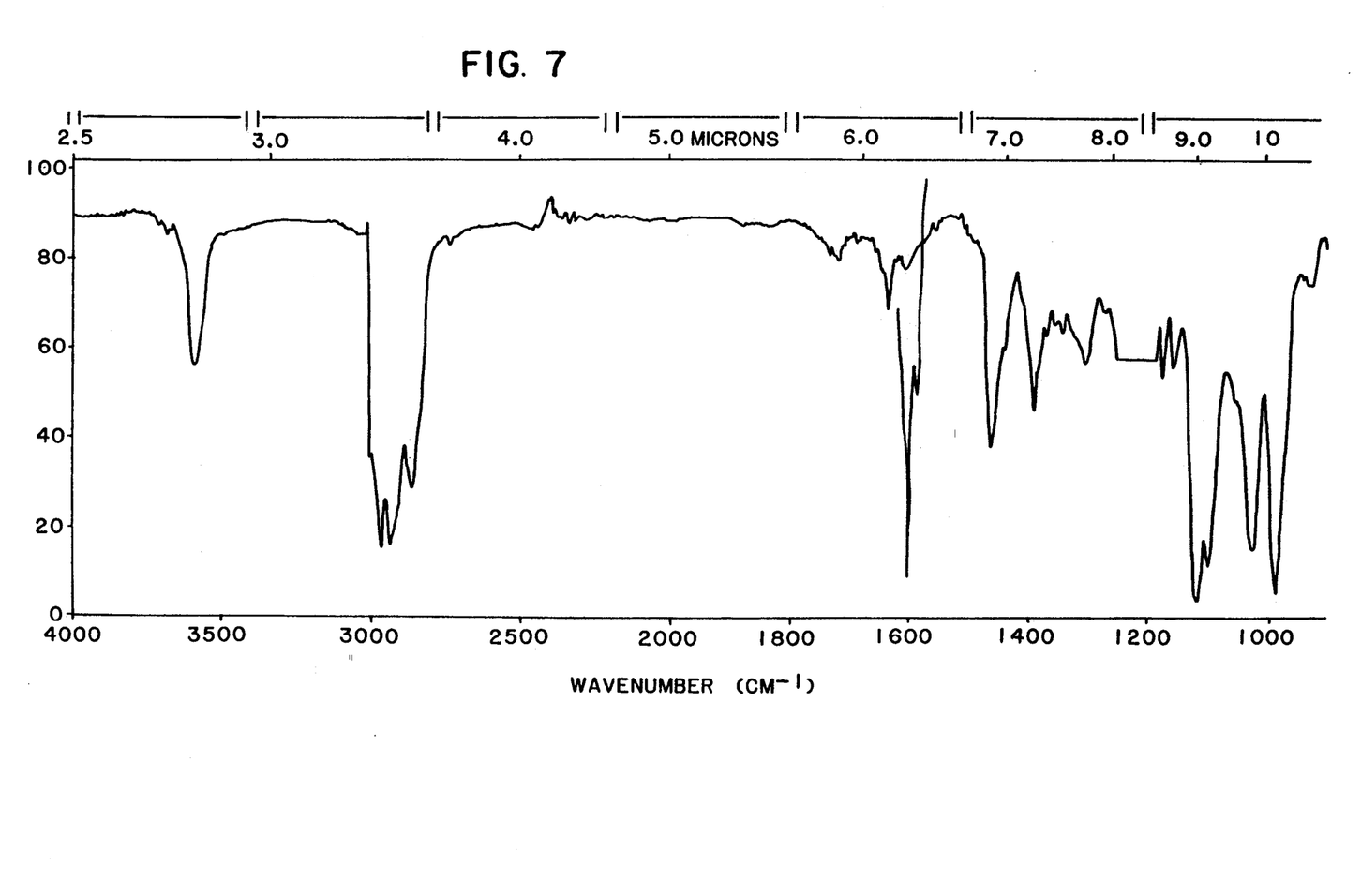
FIG. 7 is the infrared spectrum of scopularin alcohol recorded in chloroform.
Figure 8:
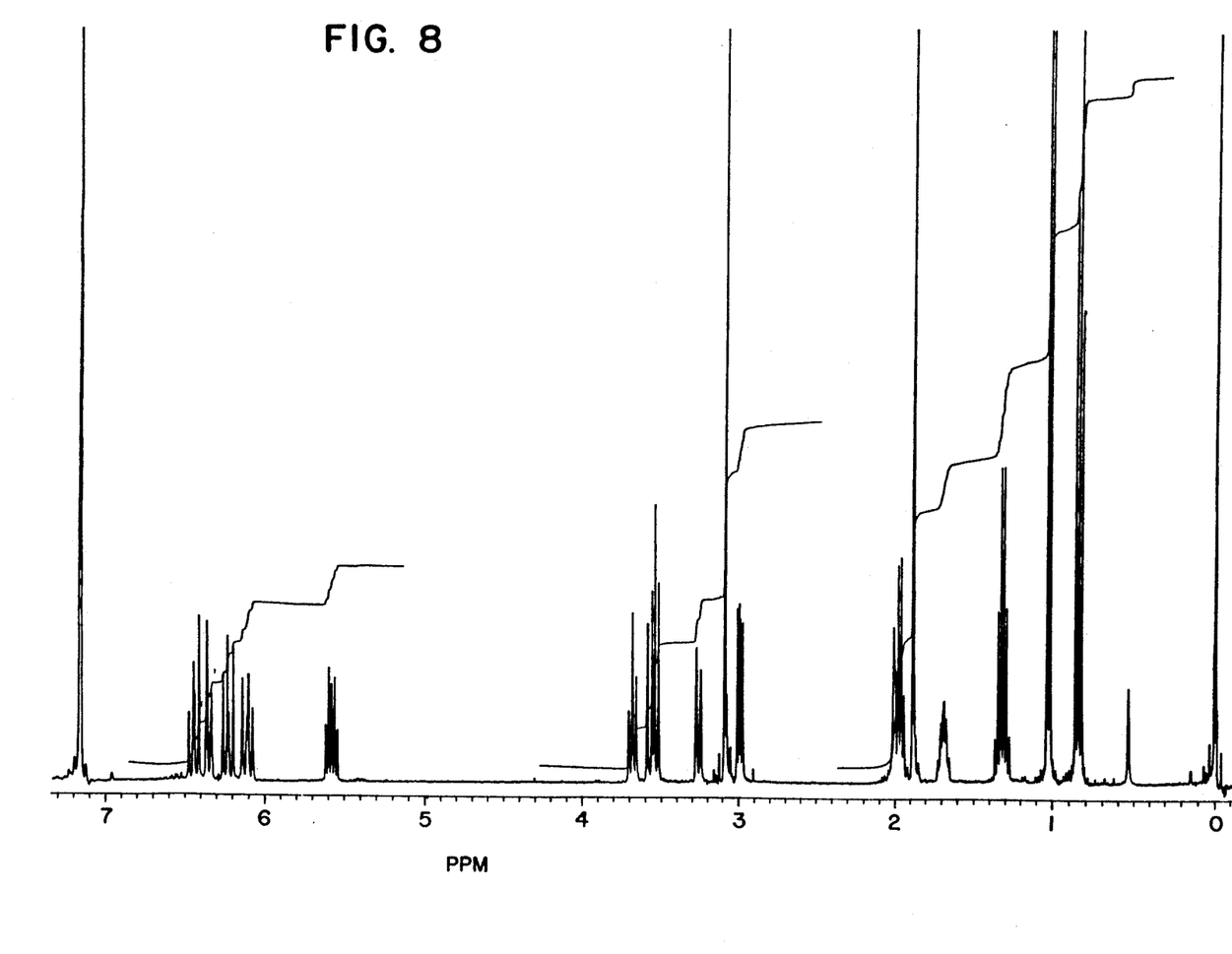
FIG. 8 is the 400 MHz $^1$H NMR spectrum of scopularin alcohol recorded in deuterobenzene.

The alcohol has the following spectral properties: The ultraviolet spectrum, shown in FIG. 6, is superimposable on the spectrum of scopularin, containing a maximum absorbance at 275 nm ($\epsilon$max 40,000), with shoulders at 266 and 286 nm. The infrared spectrum contains absorptions at 3590, 2970, 2940, 2860, 1460, 1390, 1115, 1095, 1025, 990 cm$^{-1}$. The infrared spectrum of the alcohol is shown in FIG. 7. The positive ion CI mass spectrum (not shown), contains ions consistent with the proposed molecular weight of 280 daltons, i.e. m/z  281=[M+H]$^+$,  280=[M+H−H·]$^+$ and 279=[M+H−H$_2$]$^+$. Other ions in the spectrum correspond to losses of methanol and water from the pseudomolecular ion cluster. A high resolution mass measurement of the m/z 279 ion was consistent with the composition $C_{17}H_{27}O_3$. 279=[M+H−H$_2$]$^+$=279.1965; theoretical =279.1960. This result suggests the formula $C_{17}H_{29}O_3$ for the neutral molecule. The 400 MHz $^1$H NMR spectrum of the alcohol, recorded in deuterobenzene is shown in FIG. 8. The 67 MHz $^{13}$C NMR spectrum (not shown) recorded in the same solvent contained the following resonances (ppm relative to internal TMS) 135.06, 134.77, 134.02, 131.66, 129.30, 126.97, 87.11, 84.92, 71.01, 68.65, 56.10, 35.22, 32.40, 22.84, 13.82, 11.14.

Biological Activity

The following methodology was used to determine the miniumum inhibitory concentration (hereinafter referred to as MIC) of scopularin.

The aerobic test organisms were grown in approximately 15-20 ml of Antibiotic Assay Broth (Difco) by inoculating (in tubes) the broth with a loopful of the organism from a BHI (Difco) agar slant. The inoculated tubes were incubated at 37° C. for 18 to 24 hours. These cultures are assumed to contain $10^7$ colony forming units (CFU) per ml and the cultures were diluted 1:100 to give a final inoculum level of $10^5$ CFU dilutions were made with Yeast Beef Broth (Difco).

Scopularin was dissolved in an appropriate diluent at a concentration of 1,000 μg/ml. Two-fold dilutions were made in Yeast Beef Broth (Difco), resulting in a range from 1000 μg/ml to 0.5 μg/ml. 1.5 ml of each dilution was placed into individual petri dishes to which 13.5 ml of K-10 agar was added. The composition of K-10 agar is:

| | |
|---|---|
| Beef extract | 1.5 g |
| Yeast extract | 3.0 g |
| Peptone | 6.0 g |
| Dextrose | 1.0 g |
| Agar | 15.0 g |
| Distilled Water to | 1000 ml |

The final drug concentration in the agar ranged from 100 μg/ml to 0.05 μg/ml. Organism growth control plates containing agar only were prepared and inoculated before and after the test plates. The organisms were applied to the agar surface of each plate with a Denyl Multipoint Inoculator (which delivers approximately 0.001 ml of each organism) resulting in a final inoculum of $10^4$ CFU on the agar surface.

The plates were incubated at 37° C. for 18 hours and the MICs determined. The MIC is the lowest concentration of compound inhibiting growth of the organism.

The results of the agar dilution assay are illustrated in the following tables:

TABLE 1

| Organism | SC No.* | MIC (μg/ml) Scopularin |
|---|---|---|
| Candida albicans | 5314 | 50 |
| Candida albicans | 9177 | 50 |
| Candida albicans | 11,422 | 50 |
| Candida albicans | 10,580 | 50 |
| Candida albicans | 10,102 | 100 |
| Candida albicans | 9721 | 50 |
| Candida albicans (Bacilysin$^R$)** | 12,734 | 100 |
| Candida albicans (Aculeacin$^R$) | 14,021 | 50 |
| Candida albicans | 10,584 | 25 |
| Candida albicans | 10,585 | 50 |

TABLE 1-continued

| Organism | SC No.* | MIC (μg/ml) Scopularin |
|---|---|---|
| Candida tropicalis | 8159 | 25 |
| Candida tropicalis (AmphoB$^R$) | 2963 | 6.3 |
| Candida tropicalis AmphoB$^R$ | 9861 | 25 |
| Candida tropicalis | 10,597 | 25 |
| Candida krusei (AmphoB$^R$) | 2967 | 0.4 |
| Candida krusei | 2969 | 1.6 |
| Candida krusei | 2968 | 1.6 |
| Candida parakrusei | 2621 | 0.8 |
| Candida parakrusei | 2966 | 1.6 |
| Candida pseudotropicalis | 11,241 | 25 |
| Candida guilliermondii | 2210 | 12.5 |
| Candida guilliermondii | 2996 | 0.4 |
| Candida stellatoidea | 2211 | 25 |
| Candida glabrata | 11,267 | 25 |

*SC No. is the number of the microorganism in the collection of E. R. Squibb & Sons, Inc., Princeton, New Jersey.
**$^R$represents resistance to the antibiotic named.

TABLE 2

| Organism | SC No. | MIC (μg/ml) Scopularin |
|---|---|---|
| Trichophyton mentagrophytes | 2637 | 0.2 |
| Epidermophyton floccosum | 9185 | 0.2 |
| Trichophyton rubrum | 9199 | 0.4 |
| Microsporum canis | 9237 | 0.4 |
| Aspergillus fumigatus | 2100 | 50 |

Inhibition of the Cytochrome P450 Enzyme, Lanosterol Demethylase

The inhibition of lanosterol demethylase was determined by two methods: the spectrophotometric carbon monoxide binding assay of Omura and Sato (J. Biol. Chem. 239:2370-2378, 1964) and by a radiolabeled metabolic assay.

Cells of Candida albicans, SGY677, were grown overnight without shaking at 30° C. in a medium consisting of yeast extract 1%, peptone 2%, glucose 2% and distilled water. Cells were harvested by centrifugation and resuspended in 0.65M mannitol to an optical density at 600 nm of 2.5. At this density 1 ml of cells was equal to 6.7 mg constant dry weight (105° C. for 18 hours).

Scopularin and its alcohol derivative were added to the enzyme and the inhibition of carbon monoxide binding determined over a range of give 50% inhibition of carbon monoxide binding were $3.6 \times 10^{-5}$M for scopularin and $1.4 \times 10^{-5}$M for the alcohol.

The ability of scopularin and its alcohol to inhibit the lanosterol demethylase of Candida albicans can also be visualized by a metabolic assay. Candida albicans SC5314, was grown overnight at 30° with shaking in the same medium as that used above. Cells were harvested by centrifugation and resuspended in water to give an optical density of 0.3 at 660 nm. 750 μl of this cell suspension, 300 μl of a medium containing 0.35 g Difco yeast nitrogen base without amino acids, 1 g glucose and distilled water to 10 ml, 100 μl of test material and distilled water were combined to give a final volume of 1.425 ml. This was incubated for 15 minutes at 30° C.

with shaking, then 3 μCi $^{14}$C-acetate was added and continued to incubate for 1 hour. Cells were harvested by centrifugation and extracted with 2×0.5 ml methanol; centrifuged, decanted supernate and repeated the extraction with 0.5 μl methanol-benzene (1:1). Centrifuged, decanted; combined supernates, dried and resuspended in 100 μl chloroform-methanol (1:1). The aliquots were spotted onto silica gel 60 (Merck) plates and developed chromatographically in a solvent containing dichloromethane-acetone (60:1). The plate was dried and exposed to XR-5 film (Kodak) for 2 days. The film was developed and examined for depletion of $^{14}$C-ergosterol with a corresponding increase in $^{14}$C-lanosterol by comparison with authentic standards. Both scopularin and the alcohol caused the accumulation of lanosterol, consistent with inhibition of lanosterol demethylase at concentrations of $3.6 \times 10^{-4}$M and $1.4 \times 10^{-5}$M, respectively.

What is claimed is:

1. A compound of the formula wherein R is hydrogen.

* * * * *